US008585966B2

(12) United States Patent
Abramov et al.

(10) Patent No.: US 8,585,966 B2
(45) Date of Patent: Nov. 19, 2013

(54) METHOD OF ANTIFUNGAL AND ANTIBACTERIAL DRYING OF FOOTWEAR AND AN APPARATUS FOR ELECTRO-DRYING OF FOOTWEAR

(76) Inventors: Adam Mendeleevich Abramov, Moscow (RU); Timofey Adamovich Abramov, Moscovskaya (RU)

( * ) Notice: Subject to any disclaimer, the term of this patent is extended or adjusted under 35 U.S.C. 154(b) by 859 days.

(21) Appl. No.: 11/921,280

(22) PCT Filed: May 17, 2006

(86) PCT No.: PCT/RU2006/000243
§ 371 (c)(1),
(2), (4) Date: Jun. 9, 2011

(87) PCT Pub. No.: WO2006/135273
PCT Pub. Date: Dec. 21, 2006

(65) Prior Publication Data
US 2011/0289792 A1    Dec. 1, 2011

(30) Foreign Application Priority Data

Jun. 17, 2005  (RU) ................................. 2005118823
Jul. 1, 2005    (RU) ................................. 2005120525

(51) Int. Cl.
*A61L 2/00*    (2006.01)
*C11B 1/04*    (2006.01)
(52) U.S. Cl.
USPC ........................................... 422/24; 422/308
(58) Field of Classification Search
USPC .................................................. 422/308, 24
See application file for complete search history.

(56) References Cited

U.S. PATENT DOCUMENTS

| 2,070,858 A | 2/1937 | Des Jardins et al. |
| 4,981,651 A | 1/1991 | Horng |
| 5,326,542 A | 7/1994 | Sizer et al. |

(Continued)

FOREIGN PATENT DOCUMENTS

| GB | 2399216 A   | 9/2004 |
| JP | 9075292 A   | 3/1997 |
| JP | 11056980 A  | 3/1999 |
| JP | 2002000706 A * | 1/2002 |

OTHER PUBLICATIONS

English Translation of Japanese Document No. JP 9075292 provided by the Industrial Property Digital Library: Junko, Murata; Shoes Sterilization/Drying Apparatus and Method; Mar. 25, 1997.*

(Continued)

*Primary Examiner* — Kevin Joyner
(74) *Attorney, Agent, or Firm* — The Maxham Firm

(57) ABSTRACT

This invention relates to means for footwear care and also can be used for cleansing of footwear. The method of antifungal and antibacterial drying of footwear includes simultaneous processes of heating and ultraviolet treatment, wherein optimum combination of thermal and ultraviolet treatments can be chosen. The apparatus for antifungal and antibacterial electro-drying of footwear includes heating elements (4), ultraviolet lamps (5), and two bodies (1,2). The heating element and ultraviolet lamps are disposed inside each of the bodies. Present invention provides reliable preventive care of footwear by means of coordinated simultaneous processes of heating and ultraviolet treatment.

6 Claims, 3 Drawing Sheets

(56) References Cited

U.S. PATENT DOCUMENTS

| | | | |
|---|---|---|---|
| 5,433,920 A | | 7/1995 | Sizer et al. |
| 5,835,840 A | * | 11/1998 | Goswami ................... 422/186.3 |
| 5,978,996 A | * | 11/1999 | Ullman ........................ 12/129.4 |
| 6,500,387 B1 | | 12/2002 | Bigelow |
| 6,883,197 B2 | | 4/2005 | Tak |
| 7,067,089 B2 | | 6/2006 | Wen |
| 2005/0031485 A1 | * | 2/2005 | Wen ................................ 422/28 |

OTHER PUBLICATIONS

English Translation of Japanese Document No. JP 20020007006 A provided by the Industrial Property Digital Library: Nakajima, Yaiko; Footwear Treatment Apparatus; Jan. 8, 2002.*

International Search Report (PCT/RU2006/000243) (12 pages); Written Opinion from the EPO (7 pages); International Preliminary Report on Patentability (13 pages).

* cited by examiner

METHOD OF ANTIFUNGAL AND ANTIBACTERIAL DRYING OF FOOTWEAR AND AN APPARATUS FOR ELECTRO-DRYING OF FOOTWEAR

This invention relates to the means for footwear care and also can be used for cleansing of footwear.

JP 9075292, 25 Mar. 1997, describes a method of antifungal and antibacterial drying of footwear comprising the steps of heating and ultraviolet treatment, the processes of heating and ultraviolet are carried out simultaneous during the set period of time at temperature of 60-80° C. Said method doesn't provide reliable protection of drayed articles from fungal and stable thermal exposure to treated footwear.

The main purpose of the invention is to provide simultaneous processes of drying and antifungal and antibacterial treatment of footwear.

The effect of the present method is to provide reliable antifungal and antibacterial preventive care of footwear by means of coordinated simultaneous processes of heating and ultraviolet treatment. The use of resistance heating element allows simplify the apparatus and provides necessary stable thermal exposure for simultaneous processes of heating and ultraviolet treatment of footwear.

The effect of the present invention is accomplished because of:

A method of antifungal and antibacterial drying of footwear comprising:
 heating and ultraviolet treatment,
 the processes of heating and ultraviolet treatment are carried out simultaneous during the set period of time at temperature of 60-80° C., wherein
  luminous ultraviolet intensity is 100 mCd-280 mCd,
  wavelength of ultraviolet light is 305-415 nm,
  heating is carried out by means of the resistance heating element.

JP 9075292, 25 Mar. 1997, describes an apparatus for antifungal and antibacterial electro-drying of footwear, comprising heating elements and ultraviolet lamp.

Said apparatus doesn't provide reliable protection of drayed articles from fungal and relation between heating and ultraviolet exposures.

The effect of the present apparatus is to provide reliable antifungal and antibacterial preventive care of footwear by means of coordinated simultaneous processes of heating and ultraviolet treatment. The use of resistance heating element allows simplify the apparatus and provides necessary stable thermal exposure of simultaneous processes of heating and ultraviolet treatment of footwear. Also this effect is accomplished because of apparatus body construction.

The effect of the present invention is accomplished because of:

An apparatus for antifungal and antibacterial electro-drying of footwear, comprising heating elements, ultraviolet lamps, wherein the said apparatus comprising two bodies, these bodies are made like footwear toes with ellipse back part, the heating element and the ultraviolet lamps are placed inside of the each body and fixed at low part of the body and connected together by electrical circuit, the heating elements are made resistance.

Top part of the each body has slotted openings; said slotted openings are made traversal concerning with the longitudinal axis of the body and disposed up to the resistance heating element and up to the ultraviolet lamps. Low part of the each body has slotted openings; said slotted openings are made traversal concerning with the longitudinal axis of the body and disposed below the resistance heating element.

Also the effect of the present apparatus is accomplished because of top part of the each body is transparent for ultraviolet and heat emission.

The realization possibility of present invention is substantiated by further embodiment of the apparatus and method of operation thereof.

Figure 1:
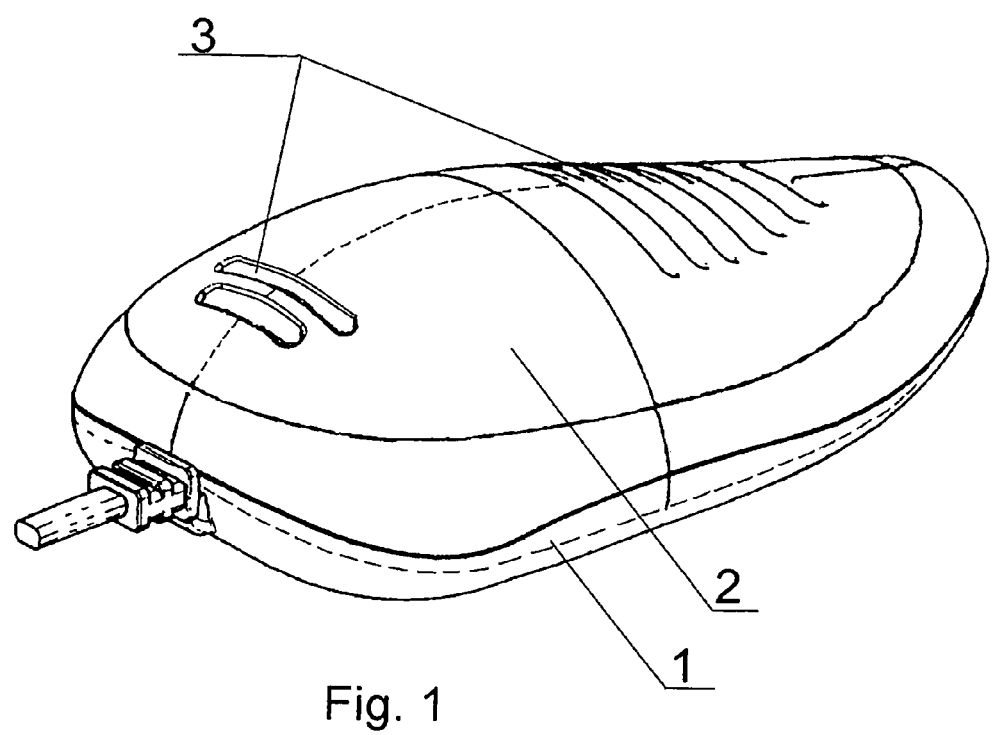
FIG. 1 shows the apparatus body (general view)

The apparatus for electro-drying of footwear includes two bodies; these bodies are made like footwear toes with ellipse back part. FIG. 1 shows general view of one of these bodies including low part 1 and top part 2. As it shown at FIG. 1 top part 2 can consist from two built-up elements. Top body part 2 has slotted openings 3. Said slotted openings 3 are made traversal concerning with the longitudinal axis of the body and disposed up to the resistance heating element 4 and up to the plate 5 with the ultraviolet lamps. Low part 1 also has slotted openings 3. Said slotted openings 3 are made traversal concerning with the longitudinal axis of the body and disposed below the resistance heating element.

Top part of the each body can be made transparent for ultraviolet and heat emission.

Figure 2:
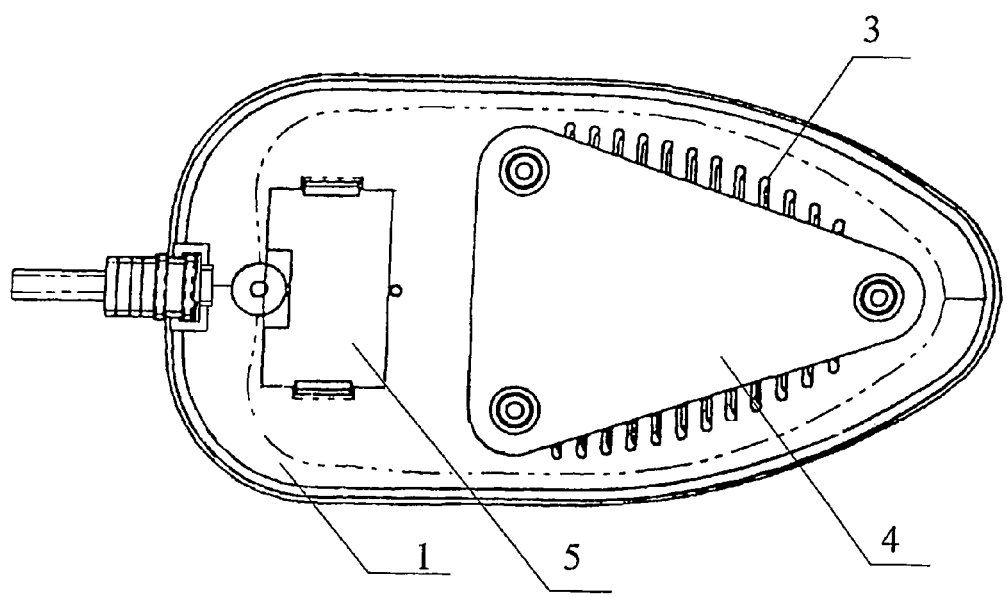
FIG. 2 shows low part of apparatus body with fixed resistance element and ultraviolet lamps (top view)

FIG. 2 shows the disposition and fixation of the resistance heating element 4 and the plate 5 with the ultraviolet lamps.

Figure 3:
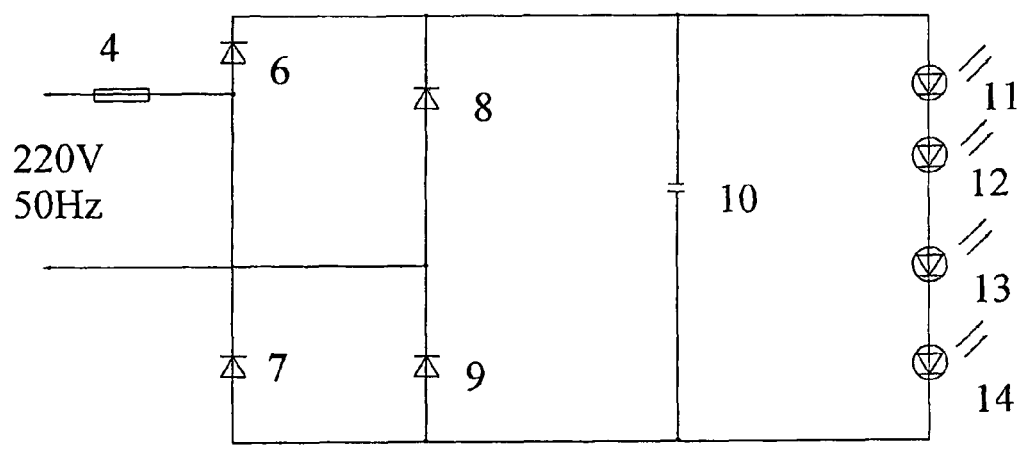
FIG. 3 shows the electrical scheme of the apparatus.

Each of the electro-drying apparatus bodies is provided of the electrical scheme (see FIG. 3), which connects the resistance heating element and the ultraviolet lamps in the each of the electro-drying apparatus bodies. Said electrical scheme comprises bridge joint made by diodes 6, 7, 8, 9. Condenser 10 and series circuit of ultraviolet lamps 11, 12, 13, 14 are parallel connected and hooked up to the first diagonal line of the bridge joint. The resistance heating element 4 and a power apparatus are connected in series and hooked up to the second diagonal line of the bridge joint.

Each of the electro-drying apparatus bodies has this electrical scheme. The electrical schemes boughs of bodies are connected by common power input.

The apparatus works in following manner.

Electric potential is supplying to the apparatus input; the switching of the resistance heating elements and ultraviolet lamps in boughs of apparatus bodies is running simultaneously, heating and ultraviolet emission acting to inner footwear surface coordinately during the time period of 5-8 h. The inner footwear surface is the subject of simultaneous processes of drying and antifungal and antibacterial treatment.

The optimal conditions of exposing to treated article was determined during the tests of the apparatus, for example during the treatment of inner footwear surface by this method within the time period of 5-8 h at temperature of 60-70° C., wherein luminous ultraviolet intensity was 150 mCd±50 mCd and wavelength of ultraviolet light was upon average 315 nm, 40-65% of bacteria and 40-65% fungal were eliminated.

During the treatment of inner footwear surface by this method within the time period of 5 h at temperature of 70-80° C., wherein luminous ultraviolet intensity was 230 mCd±50 mCd and wavelength of ultraviolet light was upon average 405 nm, 65-80% of bacteria and 40-100% fungal were eliminated

What is claimed is:

1. A method of antifungal and antibacterial drying of an inner surface of footwear, the footwear having is bottom inner surface and an enclosed toe portion, the method comprising:
 placing a housing body forming an enclosure having a top wall, a bottom wall, an ellipse back wall, and a front wall, the housing body incorporating at least one heating element and at least one ultraviolet lamp into the footwear, the housing body being shaped to generally conform to the footwear enclosed toe portion, the housing body being shaped and configured to reside on the bottom inner surface and within the enclosed toe portion of the inner footwear surface, the top wall of the housing body being comprised of material which is transparent to heat emission from the heating element;

simultaneously activating the at least one heating element and the at least one ultraviolet lamp for a set period of time, wherein:

the at least one ultraviolet lamp produces ultraviolet light with luminous ultraviolet intensity between 100 mCd-280 mCd at a wavelength of ultraviolet light between 305-415 nm; and at least one heating element is a resistance heating element which heats the inner footwear surface at a temperature between 60 degrees and 80 degrees C. for the set period of time.

2. An apparatus for antifungal and antibacterial electro-drying of an inner surface of footwear, the footwear having a bottom inner surface and an enclosed toe portion, the apparatus comprising:

a housing body forming an enclosure having a top wall, a bottom wall, an ellipse back wall, and a front wall shaped and configured to substantially conform to the enclosed toe portion of the footwear, the top wall being comprised of material which is transparent to heat emission, the bottom wall and the ellipse back wall being shaped to reside on the footwear bottom inner surface;

at least one resistance heating element enclosed within said housing body, and at least one ultraviolet lamp enclosed within said housing body and fixed to the bottom wall of the housing body in a manner to apply heat and ultraviolet light directly to the inner surface of the footwear; and an electrical circuit connecting together said at least one heating element and said at least one ultraviolet lamp.

3. The apparatus in accordance with claim 2, wherein the housing body has a longitudinal axis, and wherein the top wall of the housing body has a plurality of slotted openings, the slotted openings having a direction which is transverse to the longitudinal axis of the housing body, the slotted openings being located adjacent to the at least one resistance heating element and the at least one ultraviolet lamp.

4. The apparatus in accordance with claim 3, wherein the housing body has a longitudinal axis, and wherein the bottom wall of the housing body has slotted openings, the slotted openings having a direction which is transverse to the longitudinal axis of the housing body, and the slotted openings being located adjacent to the at least one resistance heating element.

5. The apparatus in accordance with claim 2, wherein the housing body has a longitudinal axis, and wherein the bottom wall of the housing body has slotted openings, the slotted openings having a direction which is transverse to the longitudinal axis of the housing body, and the slotted openings being located adjacent to the at least one resistance heating element.

6. The apparatus in accordance with claim 2, wherein the top wall of the housing body is transparent for ultraviolet and heat emission.

* * * * *